United States Patent [19]

Morrison

[11] 4,262,534
[45] Apr. 21, 1981

[54] LIQUID SAMPLING SYSTEM

[76] Inventor: Harold Morrison, 1406 Drexel Ave., N.E., Winter Haven, Fla. 33880

[21] Appl. No.: 43,426

[22] Filed: May 29, 1979

[51] Int. Cl.³ .......................... B01L 3/02; G01N 1/14
[52] U.S. Cl. ............................. 73/422 TC; 73/425.4 P
[58] Field of Search .......... 73/422 TC, 422 R, 423 R, 73/425.4 P

[56] References Cited

U.S. PATENT DOCUMENTS

| | | | |
|---|---|---|---|
| 2,348,806 | 5/1944 | Gillard et al. | 73/422 R |
| 3,062,055 | 11/1962 | Bills | 73/422 TC |
| 3,241,371 | 3/1966 | Horeth | 73/422 TC |
| 3,276,263 | 10/1966 | Keeney, Jr. | 73/422 TC |
| 3,726,143 | 4/1973 | Enarsson | 73/422 TC |
| 4,071,099 | 1/1979 | Hensel, Jr. | 73/425.2 F |
| 4,120,203 | 10/1978 | Clements et al. | 73/422 RF |

FOREIGN PATENT DOCUMENTS 388213  10/1973  U.S.S.R. .............................. 73/422 TC

OTHER PUBLICATIONS

Publ. "Strahman Sampling Valve", Nicolet Avenue--Florham Park, New Jersey, Figs. SV 700, 8-1960.

Primary Examiner—Daniel M. Yasich
Attorney, Agent, or Firm—Berman, Aisenberg & Platt

[57] ABSTRACT

A sampling apparatus is provided for fruit juice concentrates or other high viscosity liquids flowing in a pipeline. Small amounts of the liquid are collected automatically at preset intervals to provide a representative sample for quality control or other reasons. The sampling apparatus is designed to prevent leakage, maintain sanitation, provide reliable samples and prevent unauthorized tampering of the samples being taken.

5 Claims, 4 Drawing Figures

LIQUID SAMPLING SYSTEM

BACKGROUND OF THE INVENTION

The invention provides a means of obtaining a representative sample of orange concentrate or other high viscosity liquid from a flowing pipeline. Samples are required for quality control testing of large batches of such high viscosity liquids, e.g., those batches found in tanker loads and bulk storage tanks.

As high viscosity liquids are difficult to mix, it is necessary to take many small samples while the liquids are being loaded into appropriate receptacles; thereafter, the samples are mixed by hand for analysis in the laboratory. The controls of the liquid sampling apparatus of the present invention provide for selection of size of each sample taken as well as selection in the time interval between individual samples so that batches of various sizes may be accommodated. Also, the controls are automatically preset to terminate sampling after a specified number of individual samples have been taken to prevent overfilling of the sample container.

To provide security from tampering, a mechanical lock is provided to prevent unauthorized personnel from removing the sample container.

Since the sampling apparatus of the present invention is adapted to engage a pipeline capable of accommodating a high viscosity liquid flow, the sampling apparatus is constructed to prevent leakage from such engagement. In sampling food grade products, the present invention is advantageous since it minimizes the dead spaces in its structure, thereby reducing the chance of contamination therefrom.

DESCRIPTION OF THE INVENTION

Figure 1:
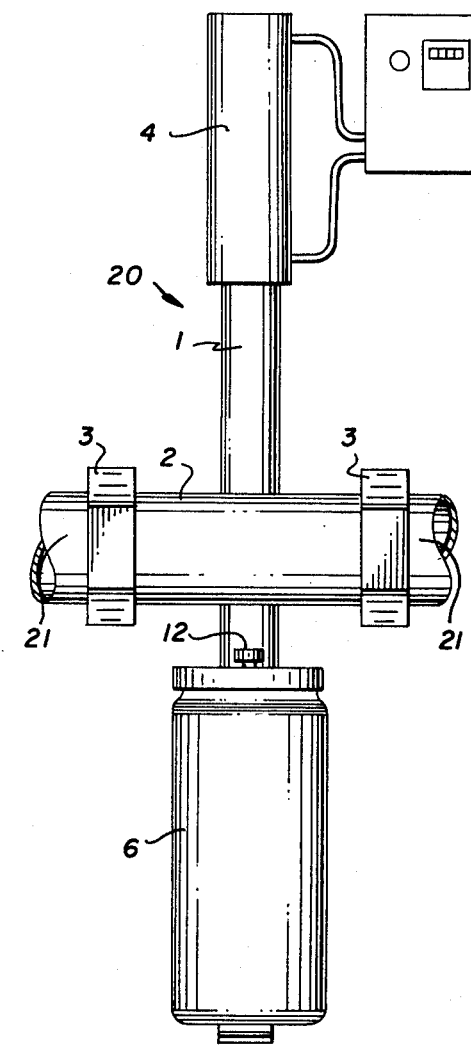
FIG. 1 is a front view of the sampling apparatus of the present invention mounted in a pipeline carrying the liquid to be sampled.

A preferred embodiment of the liquid sampling apparatus of the present invention is shown in FIGS. 1 to 4 and is designated by the reference numeral 20. Liquid sampling apparatus 20 includes a main body 1 substantially tubular in form, vertically attached to a substantially horizontally extending apertured liquid conduit 2. Apertured conduit 2 is connected into a liquid conducting pipeline by means of pipe unions 3. Main body 1 includes a passageway 23 which is in liquid communication with the aperture of conduit 2. An air cylinder operator 4 is disposed atop main body 1, with a replaceable sample collector receptacle 6 threadably engaging the bottom of main body 1. The liquid sampling apparatus 20 is operated from a control circuit enclosure 5.

Figure 2:
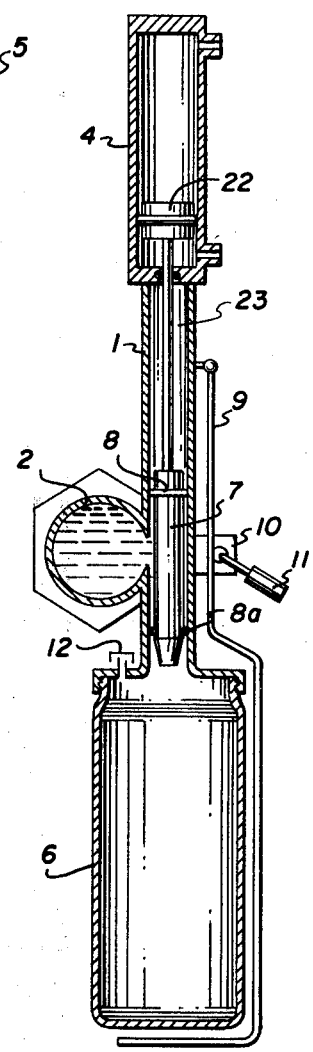
FIG. 2 is a side view of the sampling apparatus of FIG. 1 in cross section showing the position of the parts during the interval between samples.

Referring to FIG. 2, a valve plunger 7, affixed to a fluid operated piston 22 and slidable in passageway 23, is shown in its closed position. O-ring 8 is disposed about plunger 7 and sealingly engages passageway 23. O-ring 8a is disposed in the main body 1 and serves to seal passageway 23 when the plunger 7 is in its closed position. Upon plunger 7 being disposed in its closed position, liquid in the pipeline cannot pass into passageway 23; accordingly, no samples are taken when plunger 7 is in its closed position. The hinged bracket 9 and hasp 10 with padlock means 11 provide security against unauthorized removal of the sample collector receptacle 6. A vent valve 12, disposed on the bottom portion of main body 1, permits air to escape from the sample collector receptacle 6 as it fills. The vent valve 12 also prevents water or other exterior contamination from entering the sample collector receptacle 6.

Figure 3:
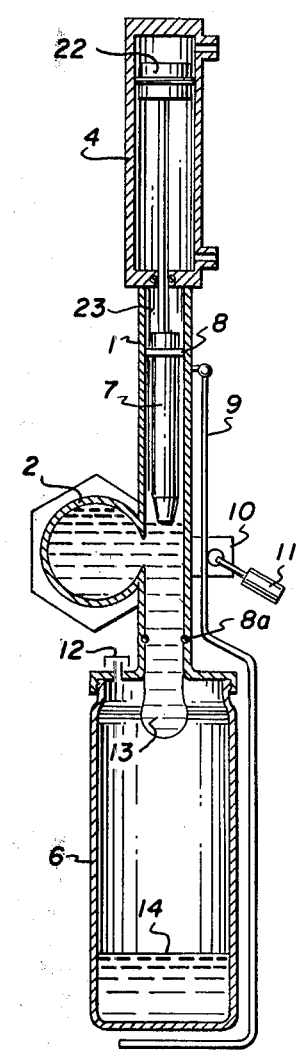
FIG. 3 is a side view of the sampling apparatus of FIG. 1 in cross section showing the position of the parts during sampling.

Referring to FIG. 3, the valve plunger 7 is shown in its open position thereby allowing a sample of liquid 13 to flow into the sample collector receptacle 6. Previously collected liquid samples 14 are shown in the sample collector receptacle 6. Plunger 7 is located in its closed or open position by actuation of piston 22.

Figure 4:
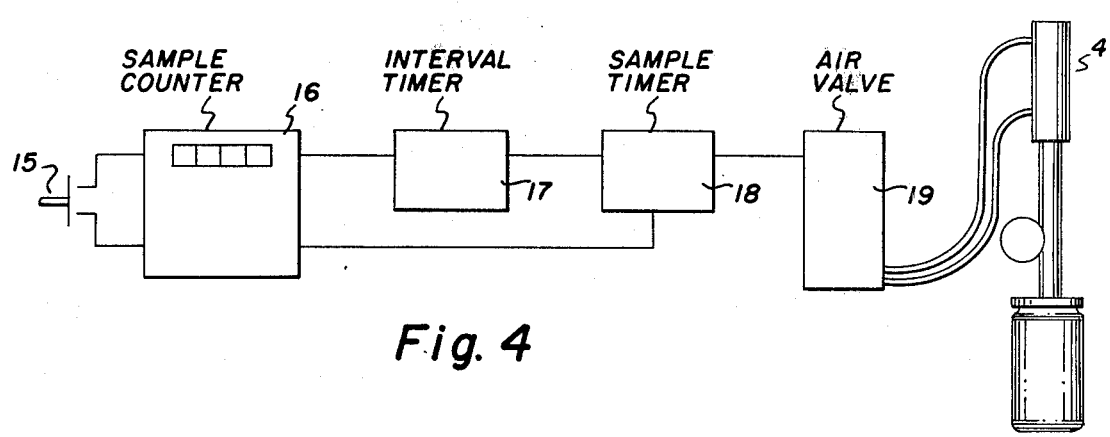
FIG. 4 is a block-diagram of typical control elements used in operating the liquid sampling apparatus of the present invention.

FIG. 4 is a block-diagram of the control system of the present invention housed in enclosed 5, which includes a reset push button 15 connected to a conventional sample counter 16 which actuates the interval timer 17. A signal from timer 17 actuates the sample timer 18 for energizing the air valve 19 to operate the air cylinder operator 4.

The sample timer 18 also actuates the sample counter 16 which counts the sample taken and continues the sample sequence. After the number of samples preset on the sample counter 16 have been completed, the sampling sequence automatically ends.

Many variations in the dimensions, position, operation and control of the liquid sampling apparatus 20 are possible without departing from the basic idea of the present invention, e.g., the air cylinder operator can be replaced by an electric solenoid or an electric motor operator. Control system logic can be reversed with the sample timer 18 preceeding the interval timer 17; and the apparatus 20 can be actuated by a pressure or flow switch rather than reset push button 15.

The liquid sampling system described can be applied to the sampling of slurries and other flowing substances.

What is claimed is:

1. A liquid sampling apparatus, comprising: a main body having a passageway therethrough, said main body vertically attached to a horizontally extending liquid conducting conduit having an aperture, said conduit adapted for communication with a pipeline and furthermore adapted to receive the flow of a liquid passing through said pipeline, said main body passageway in liquid communication with said conduit through said aperture, a receptacle removably attached to said main body below said aperture and in liquid communication with said main body passageway, a plunger axially movable within said main body passageway, means on the main body for sealingly coacting with said plunger to selectively close liquid communication from said aperture to said receptacle, means for moveably operating said plunger in said passageway thereby positioning said plunger in said passageway for opening or closing liquid communication from said aperture to said receptacle.

2. A liquid sampling apparatus according to claim 1 further comprising:
   means for lockingly securing said receptacle to said main body.

3. A liquid sampling apparatus according to claim 1 further comprising:

means for automatically controlling the number and magnitude of samples taken during a predetermined period of time.

4. A liquid sampling apparatus according to claim 1 further comprising:

a one-way valve located on said main body for venting said receptacle.

5. A liquid sampling apparatus according to claim 1 further comprising:

sealing means disposed on said plunger.

* * * * *